United States Patent
Martra et al.

(10) Patent No.: US 8,637,319 B2
(45) Date of Patent: Jan. 28, 2014

(54) METHOD AND A KIT FOR DETERMINING HUMAN OR ANIMAL BLOOD ON A SURFACE

(75) Inventors: Gianmario Martra, Bussoleno (IT); Simone Priante, Turin (IT); Marco Vincenti, Turin (IT)

(73) Assignee: Universita' Degli Studi di Torino, Turin (IT)

( * ) Notice: Subject to any disclaimer, the term of this patent is extended or adjusted under 35 U.S.C. 154(b) by 0 days.

(21) Appl. No.: 13/132,232

(22) PCT Filed: Dec. 2, 2009

(86) PCT No.: PCT/IB2009/055454
§ 371 (c)(1),
(2), (4) Date: Jun. 1, 2011

(87) PCT Pub. No.: WO2010/064199
PCT Pub. Date: Jun. 10, 2010

(65) Prior Publication Data
US 2011/0229974 A1 Sep. 22, 2011

(30) Foreign Application Priority Data

Dec. 2, 2008 (IT) .............................. TO2008A0890

(51) Int. Cl.
*G01N 33/72* (2006.01)
*G01N 33/48* (2006.01)
*G01N 21/76* (2006.01)

(52) U.S. Cl.
USPC ............... 436/66; 436/63; 436/135; 436/164; 436/166; 436/172; 422/52; 422/430; 422/82.08; 435/2; 435/810

(58) Field of Classification Search
USPC ............... 436/63, 66, 72, 135, 164, 166, 172; 422/52, 430, 68.1, 82.05, 82.08; 435/2, 435/810
See application file for complete search history.

(56) References Cited

U.S. PATENT DOCUMENTS

| 5,340,714 A | 8/1994 | Katsilometes |
| 5,679,536 A * | 10/1997 | Hayashi et al. ................ 435/7.9 |
| 2004/0022677 A1 | 2/2004 | Wohlstadter et al. |
| 2005/0176082 A1 | 8/2005 | Lefebvre-Despeaux et al. |
| 2006/0189420 A1 * | 8/2006 | Hunt ............................. 473/578 |

FOREIGN PATENT DOCUMENTS

| EP | 1624307 A2 | 2/2006 |
| WO | 03/091687 A2 | 11/2003 |
| WO | 03091687 A2 | 11/2003 |

OTHER PUBLICATIONS

Deutsche Zeischrift fur gerichtliche Medizin 57, 410-423 (1966); Die Anwendung der Chemiluminescenz des Luminols in der gerichtlichen Medizin und Toxikologie; K. Weber.
ScienceDirect; Talanta 72 (2007) 896-913; Review; Forensic application of luminol reaction as a presumptive test for latent blood detection; Filippo Barni, et al.
Police Scient; Simplified Preliminary Blood Testing; An Improved Technique and a Comparative Study of Methods; Morris Grodsky, et al.; pp. 95-104.
International Search Report for International Application No. PCT/IB2009/055454 dated Apr. 7, 2010.

* cited by examiner

*Primary Examiner* — Maureen Wallenhorst
(74) *Attorney, Agent, or Firm* — Sughrue Mion, PLLC (57) ABSTRACT

A method for detecting human or animal blood traces on a surface is described. The method is fundamentally based on the reaction of luminol and includes the preliminary operation of atomizing an inorganic powder suspension, such as titania, silica, alumina, hydroxyapatite, or the like, onto the surface to be investigated, after which a composition of luminol, a peroxidic oxidizing agent and an alkaline agent in an amount providing a pH within the range of 10 to 14, is atomized on the surface. A kit for carrying out the detection method of the invention is also described.

20 Claims, 5 Drawing Sheets

METHOD AND A KIT FOR DETERMINING HUMAN OR ANIMAL BLOOD ON A SURFACE

CROSS REFERENCE TO RELATED APPLICATIONS

This application is a National Stage of International Application No. PCT/IB2009/055454, filed Dec. 2, 2009, which claims priority from Italian Patent Application No. TO2008A000890, filed Dec. 2, 2008, the contents of all of which are incorporated herein by reference in their entirety.

BACKGROUND OF THE INVENTION

The invention refers to a method and kit for detecting human or animal blood.

The use of chemiluminescent reactions for the detection of blood traces is known from the prior art.

The term "chemiluminescence" means the emission of light that follows a chemical reaction. Among the most commonly used reagents for detecting traces of blood there is the organic molecule 5-amino-2,3-dihydro-1,4-phthalazinedione, commercially known as luminol, the oxidation of which produces chemiluminescence. This reaction is catalytically promoted by transition metal ions, including the iron ions in blood haemoglobin. Such a reaction is widely used in forensic applications, particularly for detecting the so-called latent blood traces, namely extremely low quantities of blood that are not detectable through direct observation, which may persist on various types of surfaces even after washings and/or partial removal or degradation by natural agents, detergents or agents of different nature.

In forensic applications, luminol is generally used in aqueous formulations, which comprise, besides luminol, an oxidizing agent and an alkaline agent.

The classical luminol formulations for forensic applications are the Weber/Wilson formulation, which consists of luminol, sodium or potassium hydroxide and hydrogen peroxide (K. Weber, *Dtsch Z. Gesamte Gerichtl. Med.* 57 (1966) 410-423) and the Grodsky formulation, consisting of a mixture of luminol, sodium carbonate and sodium perborate in distilled water (M. Grodsky, et al., *J. Crimin. Law Criminol. Police Sci.* 42 (1961) 95-104).

The International patent application PCT/FR2003/001299 describes a further luminol formulation, marketed with the trade name Bluestar®, comprising a luminol compound, an oxidizing agent and a base, both preferably diluted in an aqueous solvent, wherein the luminol compound is present in an amount providing a concentration from 1 to 20 mM in the final composition, the anti-oxidizing agent is hydrogen peroxide that is present in an amount providing a concentration from 25 to 100 mM in the final composition, and the base is NaOH that is present in an amount providing a concentration from 25 to 500 mM in the final composition. According to what is described in PCT/FR2003/001299, the composition allows to instantly detect extremely low amounts of blood not only under totally dark conditions but also under reduced light conditions.

Even if the luminol method is well established and widely used in forensic applications both in the United States of America and in many European countries and the use thereof has been introduced in Italy during the last decade, its performance is limited by the overall short duration of the chemiluminescent phenomenon that generally runs out within about 30 seconds (Barni, Filippo et al., *Talanta* 72 (2007) 869-913). The possibility of acquiring a correct photographic documentation of the chemiluminescent phenomenon, which is of considerable and increasing importance during the preliminary and procedural phases, is thus thwarted.

In order to overcome the drawbacks of the prior art, the present invention provides a method of detecting human or animal blood on a surface, comprising the step of applying to the surface to be investigated a liquid luminol composition comprising a luminol compound, hydrogen peroxide or other peroxidic oxidising agent and an alkaline agent in an amount providing a pH within the range of 10 to 14, characterised in that, prior to said liquid luminol composition, a suspension of inorganic powder selected from the group consisting of silicas, aluminas, titanias, alkaline metal oxides, alkaline earth metal oxides, zinc oxides, zirconias, water insoluble phosphates, micro- and nano-particles of oxide or non oxide semiconductors, functionalised derivatives thereof and mixtures containing varying proportions thereof is applied onto the surface to be investigated, wherein the inorganic powder or the functionalised derivative or the mixture are suspended in an aqueous solvent or in an organic solvent.

DETAILED DESCRIPTION OF THE INVENTION

In a preferred embodiment of the method, the inorganic powder or functionalised derivative suspension is applied to the surface to be investigated by spraying or atomization. The suspension preferably contains from 0.1 to 10 g of powder per 100 ml of solvent, depending on the powder density, the specific surface area thereof and the spraying or atomization system employed. The solvent may be an aqueous solvent, such as, for example, distilled water or a buffering system, or it may be an organic solvent, such as, for example, an alcohol, an ether, a ketone or a non-toxic hydrocarbon, such as for example cyclohexane or heptane. The suspension may further comprise additives, such as antioxidants (for example glycine, lysine or the like), designed to suppress the effect of the interferents that are present on the surface to be investigated, or chelators capable of sequestering metal interferents, with the exception of iron ions.

Silicas suitable for use in the method of the invention are both natural and synthetic silicas. Among the latter, by way of example, there can be mentioned silicas obtained by pyrolysis, sol-gel, precipitation or micro-emulsion. With regard to the aluminas, both amorphous aluminas and the crystalline, transition or corundum-type (α) ones are suitable for use in the method of the invention. Among the titanias suitable for use in the method of the invention, there are cited the amorphous and crystalline ones in rutile, anatase, brookite phases, for instance manufactured through pyrolysis, sol-gel, precipitation or micro-emulsion, as well as titanias various in nature and mixtures thereof. Phosphates suitable for use in the method of the invention are those insoluble in the solvent used, such as for example water. Among the water-insoluble phosphates, naturally occurring or synthetic calcium phosphates (for example, hydroxyapatites) are cited by way of example. Among the latter, those generated, for example, by neutralization or by dual exchange are cited. Zinc oxides and zirconias suitable for use in the method of the invention are both the amorphous and the crystalline ones. Finally, among the micro- and nano-particles of oxide or non oxide semiconductors, CdS, CdSe, Si, $Ta_3N_5$ and TaON are cited by way of example.

All the above-mentioned inorganic powders can optionally be functionalised with metal cations (for example Co, Cr, etc.), organic or inorganic anions (for example sulphides, fluorides, nitrides, carbides), metal particles, organic molecules or organo-metallic complexes.

As will be detailed in the following realization examples, the spraying or atomization of the inorganic powder or functionalised derivative suspension onto the surface to be investigated, prior to the application of the liquid luminol composition, surprisingly and advantageously induces an amplification of the chemiluminescence phenomenon, which is increased both in intensity and duration, until it is made visible to the human eye for an extremely long period of time, up to about 15 minutes from the start of the reaction.

The chemiluminescence amplification phenomenon induced by luminol oxidation has been experimentally observed by the present inventors with various luminol formulations that are described in the literature, among which there are particularly cited the Weber/Wilson formulation and the Bluestar® kit, which exhibit the common feature of containing hydrogen peroxide as the oxidizing agent. Therefore, the inventors believe that the chemiluminescence amplification phenomenon occurs with any luminol formulation, the oxidizing agent of which is hydrogen peroxide or other peroxide, in any liquid or solid form. As described in the patent application, the addiction product of $H_2O_2$ and urea named "Urea Adduct", for example available from Sigma-Aldrich as a powder or as lozenges, can be a source of hydrogen peroxide suitable for use in the kit of the invention.

The term "luminol compound", as used in the scope of the present description, includes not only the organic molecule 5-amino-2,3-dihydro-1,4-phthalazinedione (luminol), but all the isomers, derivatives, polymers and precursors thereof capable of emitting chemiluminescence upon oxidation catalysed by the iron ions of haemoglobin. Among the luminol derivatives suitable for use in the method of the invention, ethyl-luminol and diethyl-luminol are cited by way of example; conformational isomers and configurational isomers are cited by way of example among the isomers.

In a preferred embodiment of the method, the liquid luminol composition used in the method of the invention comprises:
  luminol at a concentration from 0.01 mM to 4 mM;
  hydrogen peroxide at a concentration from 1 mM to 20 mM; and
  sodium or potassium hydroxide at a concentration from 0.01 mM to 400 mM.
  Preferably, the solvent is deionized or distilled water.

The liquid luminol composition is preferably applied to the surface to be investigated by spraying or atomization. It is preferable to let the previously atomized powder suspension air-dry before applying the liquid luminol composition.

A second object of the invention is a kit for detecting human or animal blood on a surface, comprising:

in at least one first vessel, a luminol formulation comprising a luminol compound, hydrogen peroxide or other peroxidic oxidising agent, and an alkaline agent in an amount providing a pH within the range of 10 to 14; and
  in at least one second vessel, a predetermined amount of an inorganic powder selected from the group consisting of silicas, aluminas, titanias, alkaline metal oxides, alkaline earth metal oxides, zinc oxides, zirconias, water insoluble phosphates, micro- and nano-particles of oxide or non oxide semiconductors, functionalised derivatives thereof and mixtures containing varying proportions thereof.

The kit according to this embodiment can also comprise a further vessel containing a predetermined volume of an aqueous or organic solvent suitable for the manufacture of the powder suspension, or containing a predetermined amount of the reagents required for the manufacture of a buffering solution.

In an alternative embodiment, the kit of the invention comprises:
  in at least one first vessel, a luminol formulation comprising a luminol compound, hydrogen peroxide or other peroxidic oxidising agent, and an alkaline agent in an amount providing a pH within the range of 10 to 14; and
  in at least one second vessel, a suspension of inorganic powder selected from the group consisting of silicas, aluminas, titanias, alkaline metal oxides, alkaline earth metal oxides, zinc oxides, zirconias, water insoluble phosphates, micro- and nano-particles of oxide or non oxide semiconductors, functionalised derivatives thereof and mixtures containing varying proportions thereof, wherein the inorganic powder, the functionalised derivative or the mixture are suspended in an aqueous solvent or an organic solvent.

The kit of the invention can include any luminol formulation, provided that the oxidising agent is a peroxidic compound, such as for example hydrogen peroxide. The Weber/Wilson formulation described in K. Weber, *Dtsch Z. Gesamte Gerichtl. Med.* 57 (1966) 410-423) and the formulations described in the patent application PCT/FR2003/001299 are cited by way of example, which have in common the fact of comprising a luminol compound, a peroxidic oxidising agent, and an alkaline agent, such as for example NaOH or KOH.

As described in PCT/FR2003/001299, the three main components of the luminol formulation (that is, luminol compound, peroxidic oxidising agent, and alkaline agent) may be provided in a liquid or solid form, for instance in the form of a powder or lozenges. This is the reason why, when referring to the kit, the expression "luminol formulation" is used instead of the expression "liquid luminol composition" previously used when referring to the detection method.

In a first variant of the kit of the invention, the three main components of the luminol formulation are provided in one single pre-mixture, in a formulation suitable for preventing premature reactions to occur, the accomplishment of which is within the abilities of the person of ordinary skill in the art.

In a second variant of the kit of the invention, the three main components of the luminol formulation are provided in two separate vessels, one of which contains a pre-mixture of the luminol compound and the oxidising or the alkaline agent, whilst the other contains the alkaline or the oxidising agent not included in the pre-mixture.

In a third variant of the kit of the invention, the three main components of the luminol formulation are provided in three separate vessels, one of which contains the luminol compound, another one the oxidising agent, and still another one the alkaline agent.

According to a preferred embodiment of all of the above-described variants, the luminol formulation comprises:

luminol in an amount providing a concentration of 0.01 mM to 4 mM in the final composition, hydrogen peroxide in an amount providing a concentration of 1 mM to 20 mM in the final composition, and sodium or potassium hydroxide in an amount providing a concentration of 0.01 mM to 400 mM in the final composition.

As regards the type of vessels usable in the kit of the invention, any of the per se known vessel types can be used, for instance for the packaging of chemical reagents, drugs or foodstuffs.

For reagents in a liquid form, resealable glass or plastic vessels may conveniently be used, such as for example bottles, vials, flasks.

For reagents in a solid form, for instance in the form of a lozenge or powder, sachets or blisters fitted with cavities may conveniently be used, each sachet or cavity being suitable to accommodate a single dose of reagent.

However, any type of vessel that is suitable for the specific considered reagent may be chosen, the correct choice and use thereof are within the abilities of the person of ordinary skill in the art and thus will not be described in further detail as they are not a specific object of the present invention.

The following examples are given solely by way of illustration and are not intended as limiting the scope of the invention, as defined in the appended claims. The claims are an integral part of the description.

EXAMPLES

Example 1

Phenomenological Observations

In order to assess the effectiveness of the method of the invention in amplifying the chemiluminescence phenomenon caused by luminol oxidation, the following has been carried out.

A classical luminol formulation was prepared according to Weber\Wilson, following the operational protocol that follows:

1. Weigh 8 g of hydroxide sodium and dissolve it in 500 ml of deionized water [0.4 N] (solution A)
2. Dilute 10 ml of $H_2O_2$ in 490 ml of deionized water [0.176 M] (solution B)
3. Weigh 0.354 g of luminol and dissolve it in 62.5 ml of solution A, adjust to a final volume of 500 ml (solution C)
4. Store the solutions at 4° C. and in the dark until use.
5. At the time of use, in a commercial atomizer, prepare the test solution with 10 ml of solution A+10 ml of solution B+10 ml of solution C; adjust to a volume of 100 ml with deionized water.

The so prepared Weber/Wilson formulation was used for haemoglobin detection at 1\1000 dilution with PBS (phosphate buffered saline), as compared to the normal physiological concentration in human blood (15 g/100 ml). The diluted haemoglobin was placed onto a glass surface. The following suspensions of inorganic powders in phosphate buffer were atomized onto the surface to be investigated:

pyrogenic silica $1.4 \times 10^{-3}$ g/ml;
pyrogenic alumina $6.99 \times 10^{-4}$ g/ml;
commercial hydroxyapatite (Biorad) $1.16 \times 10^{-3}$ g/ml;
synthetic hydroxyapatite $1.16 \times 10^{-3}$ g/ml;
$TiO_2$ Anatase/Rutile (50 $m^2$/g) $1.4 \times 10^{-3}$ g/ml;
$TiO_2$ Anatase (10 $m^2$/g) $6.7 \times 10^{-3}$ g/ml.

The powders were used in amounts such that, for each powder, the quantity of haemoglobin in the solution was able to cover, as a theoretical monolayer, the whole surface of the powder used, assuming that the protein settles onto the surface according to the "side-on" configuration.

The above-described suspensions were atomized onto the surface to be investigated by a normal commercial atomizer and were left to air-dry for about 30 minutes, after which the luminol formulation was atomized and the emitted chemiluminescence was observed in complete darkness.

For a comparison, the same procedure was carried out with the luminol formulation alone.

Figure 1:
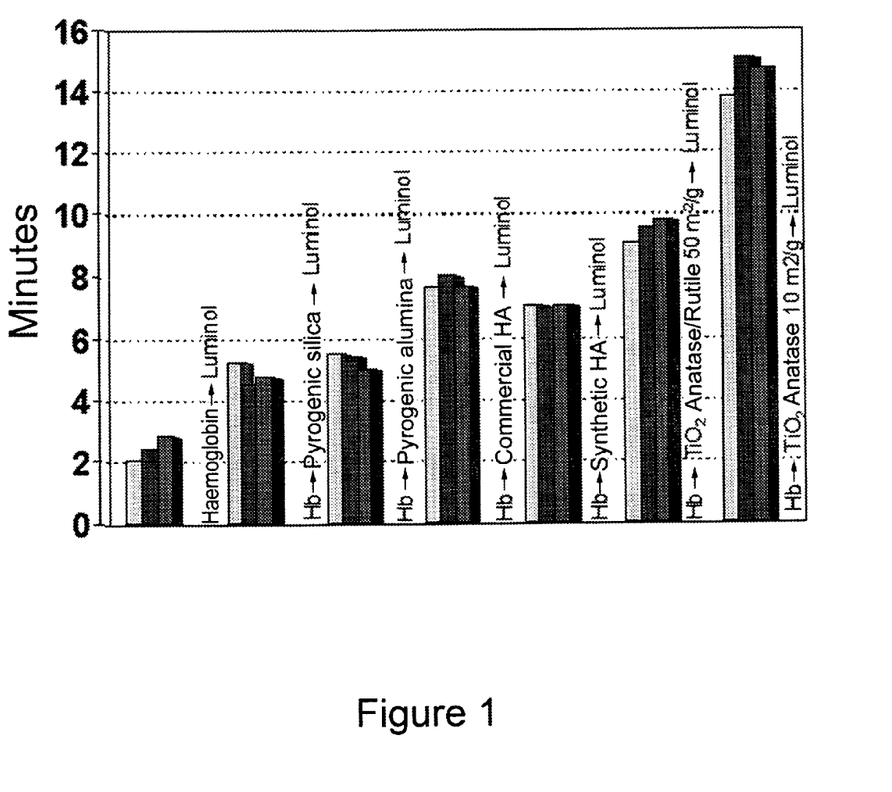
FIG. 1 is a histogram graph showing the duration of chemiluminescence induced by luminol reaction in a number of tests carried out with different inorganic powders, compared to luminol alone. Each test was carried out in triplicate.

The data from the phenomenological observations (duration of the chemiluminescence induced by luminol reaction) are shown in FIG. 1. Each test was carried out at least in triplicate.

Example 2

Quantitative Study

A quantitative detection of the chemiluminescence emission was performed by using a spectrofluorometer capable of collecting and representing, as a function of time, the photons emitted from the radioactive decay of the products from the luminol oxidation reaction.

The tests were carried out by depositing 10 μl haemoglobin spots, diluted 1/1000 in phosphate buffer (pH 7.4), onto glass Petri dishes, letting them air-dry for about 30 minutes, subsequently atomizing thereon the inorganic powder suspensions referred to in Example 1, and finally atomizing 10 μl of luminol in Weber/Wilson formulation, prepared as describe in Example 1.

As to the number of photons per second emitted at time zero, up to 10-fold increases in chemiluminescence were recorded. In addition, a signal clearly distinguishable from the background noise was registered for up to approximately 10 minutes.

The difference in the length of time during which the chemiluminescence was visible between the first phenomenological observations in Example 1 and the quantitative measurements in the present example is ascribable to the different (non-linear) dynamic range of the human eye in comparison with the fluorometer detector.

Example 3

Simulation of a Real Case

A field test was performed for the adopted procedure, a photographic record of which was collected by using a Reflex Canon EOS 400D and a 50 mm objective.

The collected photographic record refers to the detection of two series of latent blood traces obtained by depositing onto two glass plates (thoroughly washed so as to eliminate any traces of interfering oxidizing material) a few drops of blood collected from a donor, subsequently air-dried for 1 minute and then washed by using a water-soaked cotton wool plug.

One of the two plates was then atomized with an aqueous suspension of $TiO_2$ Anatase (10 $m^2$/g) (0.7 g titanium dioxide in 50 ml deionized water, dispersed by ultrasounds for 5 minutes), which was left to dry for 30 minutes.

The images were acquired in the dark upon atomization of a luminol solution prepared according to Example 1.

It has been possible to verify that, as in the case of the plate treated with the $TiO_2$ suspension (titanium dioxide, also known as "titania"), the light emission initially results decidedly more intense and well observable and documentable even at 5 minutes from the beginning of the phenomenon, which instead appears already very faint after about 1 minute in the case of the plate not treated with the powder suspension and disappears completely after 3 minutes.

Obviously, control tests were performed, which demonstrated absence of chemiluminescence upon atomization of the luminol solution onto titania alone (without blood).

Interestingly, the atomization onto the latent blood traces with a luminol solution (Wilson/Weber formulation) containing suspended inorganic particles gave no improvement of the effect.

Example 4

Comparison with the Kit Bluestar®

In order to verify if the method of the invention is also competitive in comparison with the Bluestar® kit, a crime scene was simulated wherein two blood stains, caused by vertical dripping (from a short distance) of human whole blood (500 µl) onto a tiled floor, were thoroughly washed with water after 5 minutes, repeating the washing operation several times, so as to eliminate every visible trace. For the photographic documentation, a Reflex camera (Canon EOS400D) standing on a tripod orthogonally oriented towards the pavement was used.

The search for haematic material on the support was performed in parallel by using the method of the invention as described in Example 3 (left tile) or the commercial Bluestar® kit (right tile). The tiles were chosen randomly.

The pictures were taken immediately after atomizing the luminol-containing composition (time "0") and then at 30 and 60 seconds from the start of the luminol reaction.

Exposure settings (Reflex Canon EOS 400D camera): ISO 400, ESP 0, opening of the shutter 6". The pictures are not shown herein.

At the time of the atomization of the luminol-containing composition, no substantial differences are detectable in the pictures between the two procedures used. In contrast, after the first 30 seconds, the chemiluminescence generated by the method of the invention appears much more intense compared to the one generated by using the Bluestar® kit alone. The chemiluminescence generated with the Bluestar® kit alone results poorly visible already after 30 seconds. After 60 seconds, a blue halo is still detectable in the picture of the tile treated according to the method of the invention, whereas no chemiluminescence is visible any more in the picture of the tile treated with the Bluestar® kit alone.

Example 5

Assessment of Absence of Interference with the Extraction Procedures and DNA Typing We verified if the method of the invention would interfere with the extraction and typing procedures for genetic material associated with a blood trace.

To that end, 5 ml of venous blood were collected from a male donor by using a tube without any anticoagulant additive. A 1:10 dilution with physiological solution was prepared from the whole blood. Four samplings (10 µl each) of such a dilution were placed onto a glass plate with the aid of a laboratory pipette. The blood stains were left to dry at room temperature for 24 hours. Then, we atomized a fraction of the traces with luminol, another fraction only with a $TiO_2$ Anatase (10 m²/g) suspension (1 g/100 ml) dispersed in phosphate buffer (pH 7.4) by applying ultrasounds for 5 minutes, and still another fraction firstly with the aforesaid suspension and then with luminol, according to the scheme shown below:

[A]—BLOOD 1/10

[B]—BLOOD 1/10+LUMINOL

[C]—BLOOD 1/10+SUSPENSION

[D]—BLOOD 1/10+SUSPENSION+LUMINOL

The so-treated samples were left to dry at room temperature and then were completely removed from the glass plate by using sterile plugs soaked with physiological solution.

The plugs were led to the laboratory procedures required for DNA extraction and typing of the genetic profile.

The DNA was isolated from the plugs after lysis of the material in 200 µl of FBL buffer (Macherey-Nagel) and 20 µl of proteinase K (20 mg/ml) (Macherey-Nagel). The so-obtained product was incubated at 56° C. overnight. Subsequently, the DNA in the samples was isolated from the other cell components by absorption onto silica-coated magnetic microspheres in the presence of chaotropic salts by using Mag blood 96 Nucleus (Macherey-Nagel) coupled to KingFisher automatic extractor (ThermoLabsystems). The final elution volume of the extracts was 60 µl.

The quantification of the human genomic DNA present in the extracts was carried out by hybridization with a TaqMan probe specific for an intron region of the reverse transcriptase gene from human telomerase by using the Quantifiler Human DNA Quantification kit (Applied Biosystems) and the instrument 7300 Real time PCR system (Applied Biosystems). The real-time PCR was performed in a final volume of 12.5 µl containing 2 µl of the extracts to be quantified, 5.25 µl of Quantifiler Human Primer Mix (Applied Biosystems) and 6.25 µl of Quantifiler PCR Reaction Mix. The thermal profile of the amplification contemplated an initial denaturation step at 95° C. for 10 minutes, followed by 40 cycles consisting of denaturation at 95° C. for 15 seconds and annealing/extension at 60° C. for 1 minute. The analytical parameters used in the data processing were the following: fluorescence intensity for CT definition 0.2; range for the baseline definition comprised between cycles 3 and 15 of the PCR. For the construction of the standard curve, serial dilutions in duplicate of human DNA were used, with a concentration from 50 ng/µl to 0.023 ng/µl. The quantification of each sample was performed in triplicate.

The samples A, B, C and D were analysed for nuclear DNA polymorphisms, by co-amplification of the polymorphic loci indicated below, by using the commercial "AmpFISTR Identifiler" kit (Applied Biosystems):

(i) Amelogenin locus for gender identification. The Amelogenin gene is located on both of the sex chromosomes, X (Xp22.1-22.3) and Y (Yp11.2), but on chromosome X, at the level of the first intron, it exhibits a six-base pair deletion; it follows that, in the presence of male-derived biological material (XY), the PCR reaction generates two amplification products with different sizes; instead, in a female sample (XX), the PCR produces one amplified product only.

(ii) 15 microsatellites (short tandem repeats, STRs) with a tetranucleotide pattern, the salient features of which are summarized in the table below.

| Locus | Chromosome location | Main alleles |
|---|---|---|
| D8S1179 | 8q | 8, 9, 10, 11, 12, 13, 14, 15, 16, 17, 18, 19 |
| D21S11 | 21q11.2-q21 | 24, 24.2, 25, 26, 27, 28, 28.2, 29, 29.2, 30, 30.2, 31, 31.2, 32, 32.2, 33, 33.2, 34, 34.2, 35, 35.2, 36, 37, 38 |
| D7S820 | 7q11.21-22 | 6, 7, 8, 9, 10, 11, 12, 13, 14, 15 |
| CSF1PO | 5q33.3-34 | 6, 7, 8, 9, 10, 11, 12, 13, 14, 15 |
| D3S1358 | 3p | 12, 13, 14, 15, 16, 17, 18, 19 |
| TH01 | 11p15.5 | 4, 5, 6, 7, 8, 9, 9.3, 10, 11, 13.3 |
| D13S317 | 13q22-31 | 8, 9, 10, 11, 12, 13, 14, 15 |
| D16S539 | 16q24-qter | 5, 8, 9, 10, 11, 12, 13, 14, 15 |
| D2S1338 | 2q35-37.1 | 15, 16, 17, 18, 19, 20, 21, 22, 23, 24, 25, 26, 27, 28 |
| D19S433 | 19q12-13.1 | 9, 10, 11, 12, 12.2, 13, 13.2, 14, 14.2, 15, 15.2, 16, 16.2, 17, 17.2 |
| vWA | 12p12-pter | 11, 12, 13, 14, 15, 16, 17, 18, 19, 20, 21, 22, 23, 24 |
| TPOX | 2p23-2per | 6, 7, 8, 9, 10, 11, 12, 13 |
| D18S51 | 18q21.3 | 7, 9, 10, 10.2, 11, 12, 13, 13.2, 14, 14.2, 15, 16, 17, 18, 19, 20, 21, 22, 23, 24, 25, 26, 27 |
| D5S818 | 5q21-31 | 7, 8, 9, 10, 11, 12, 13, 14, 15, 16 |
| FGA | 4q28 | 17, 18, 19, 20, 21, 22, 23, 24, 25, 26, 26.2, 27, 28, 29, 30, 30.2, 31.2, 32.2, 33.2, 42.2, 43.2, 44.2, 45.2, 46.2, 47.2, 48.2, 50.2, 51.2 |

From 1 to 5 μl of DNA, depending on the results from the absolute quantification, were amplified in a final volume of 12.5 μl according to the manufacturer's directions. The thermal amplification profile used contemplated an initial denaturation at 95° C. for 15 minutes, followed by 28 cycles consisting of denaturation at 94° C. for 1 minute, annealing at 59° C. for 1 minute, extension at 72° C. for 30 seconds, and by a final extension at 60° C. for 1 hour. The resolution of the amplified products was carried out by capillary electrophoresis (ABI PRISM 310 Genetic Analyzer—Applied Biosystems). For the analysis of the electrophoretic data, the GeneScan and Genotyper 3.7 software (Applied Biosystems) were used.

The data related to the DNA concentration in ng/μl in each extract (in triplicate: α; β; γ), the values of which are indicated in the following table, were derived from the quantification of the genetic material present in the blood traces.

The total volume of each sample is 60 μl, but only 10 μl of this volume can be used for coamplifying the polymorphic loci useful for the "construction" of the genetic profile. For instrumental reasons, only samples having DNA concentrations of 0.02 ng/μl (that is 0.2 ng in 10 μl) or more are usable for judicial purposes in order to obtain a valid profile for further comparative investigation. In fact, interpretation results difficult and not objective any more below this cut-off threshold.

| Sample | α [ng/μl] | β [ng/μl] | γ [ng/μl] | Average |
|---|---|---|---|---|
| A | 0.539 | 0.526 | 0.495 | 0.520 |
| B | 0.396 | 0.379 | 0.265 | 0.337 |
| C | 0.776 | 1.083 | 0.948 | 0.936 |
| D | 0.753 | 0.971 | 0.913 | 0.879 |

It is important to point out that each of the assayed samples A, B, C and D only contains 1 μl of blood. Detection of such a low amount of blood is extremely difficult in a crime scene. Therefore, these samples represent limit conditions that can be encountered in forensic investigations.

On analysing the obtained results, the titania Anatose suspension (10 m$^2$/g) appears to give no interference with the DNA extraction and amplification procedure. The higher concentration values from the suspension-treated spots may be explained by a better recovery of DNA during the extraction procedure, due to the high surface area of such particles compared to the support on which the spots have been deposited.

The DNA from the four samples referred to above was then typed by amplification and comparison of the 15 microsatellites STR CODIS and the Amelogenin locus, in order to assess if the contact with titanium dioxide could have modified the electrophoretic mobility and molecular weight thereof.

Figure 2:
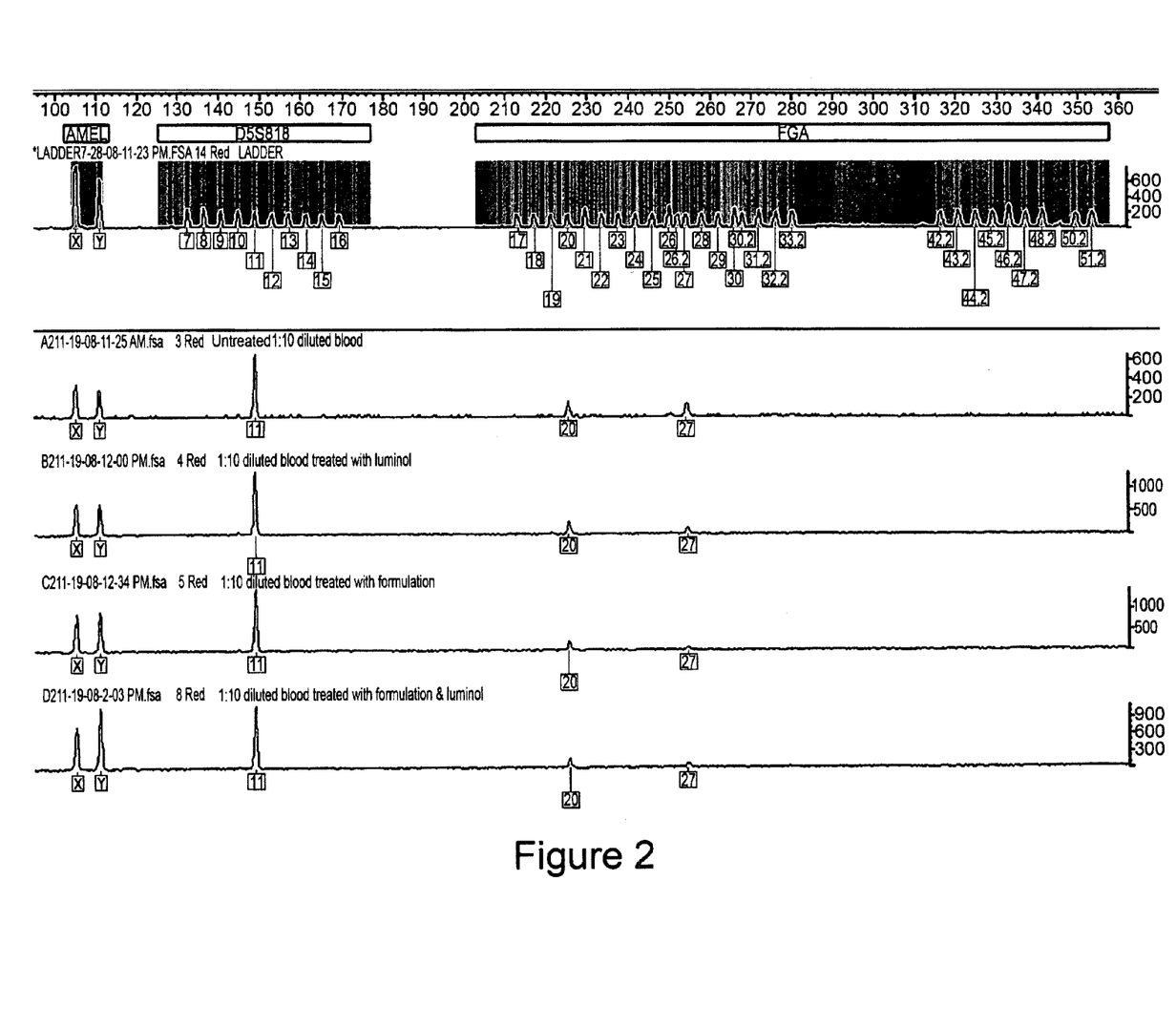
FIG. 2 shows the results of nuclear DNA polymorphism analysis carried out on samples A (blood 1/10); B (blood 1/10+luminol); C (blood 1/10+TiO2 Anatase suspension); and D (blood 1/10+TiO2 Anatase suspension+luminol); locus: Amelogenin; D5S818; FGA.
Figure 3:
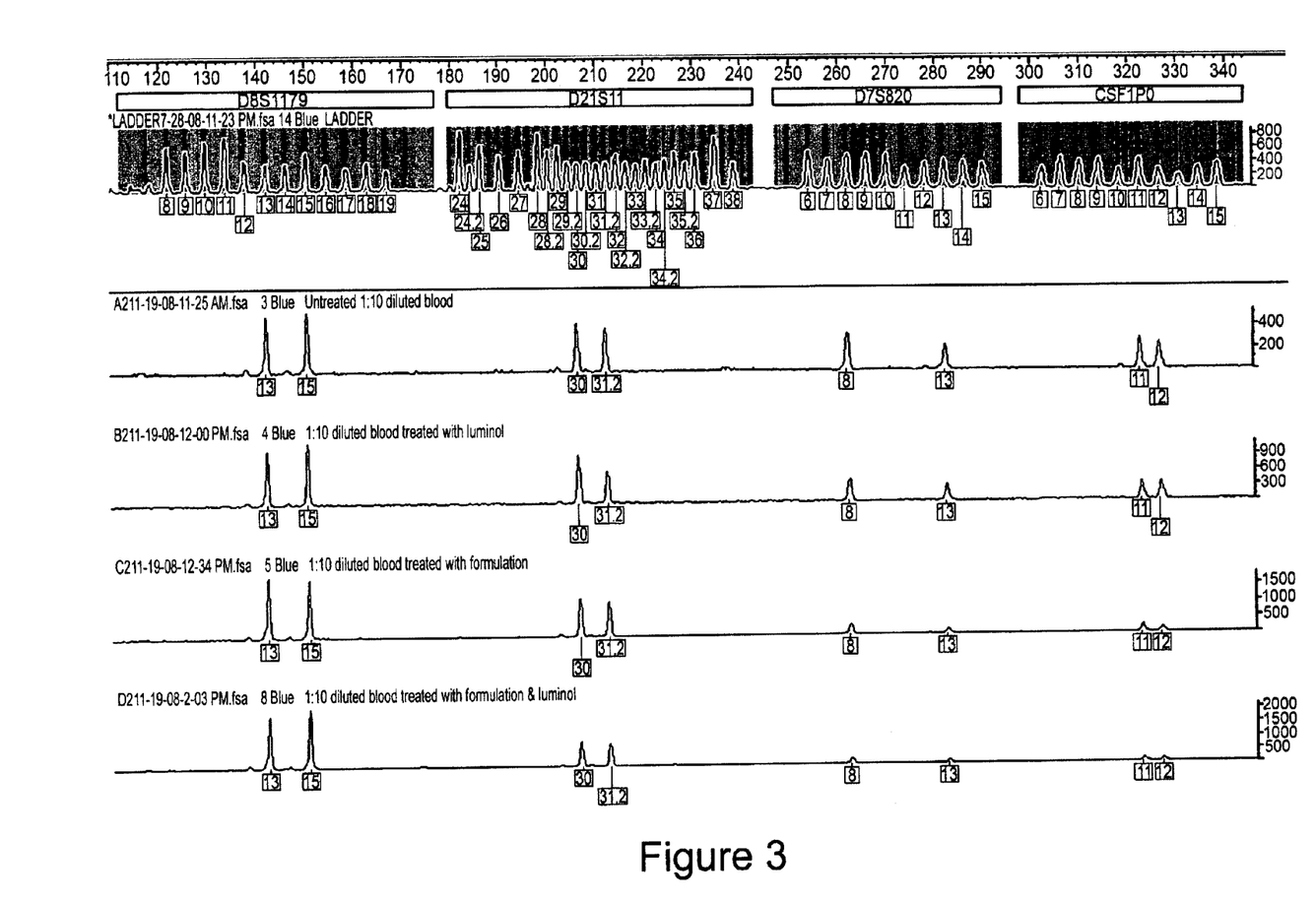
FIG. 3 shows the comparison of the electrophoretic runs of samples A; B; C; D; locus: D861179; D21S11.
Figure 4:
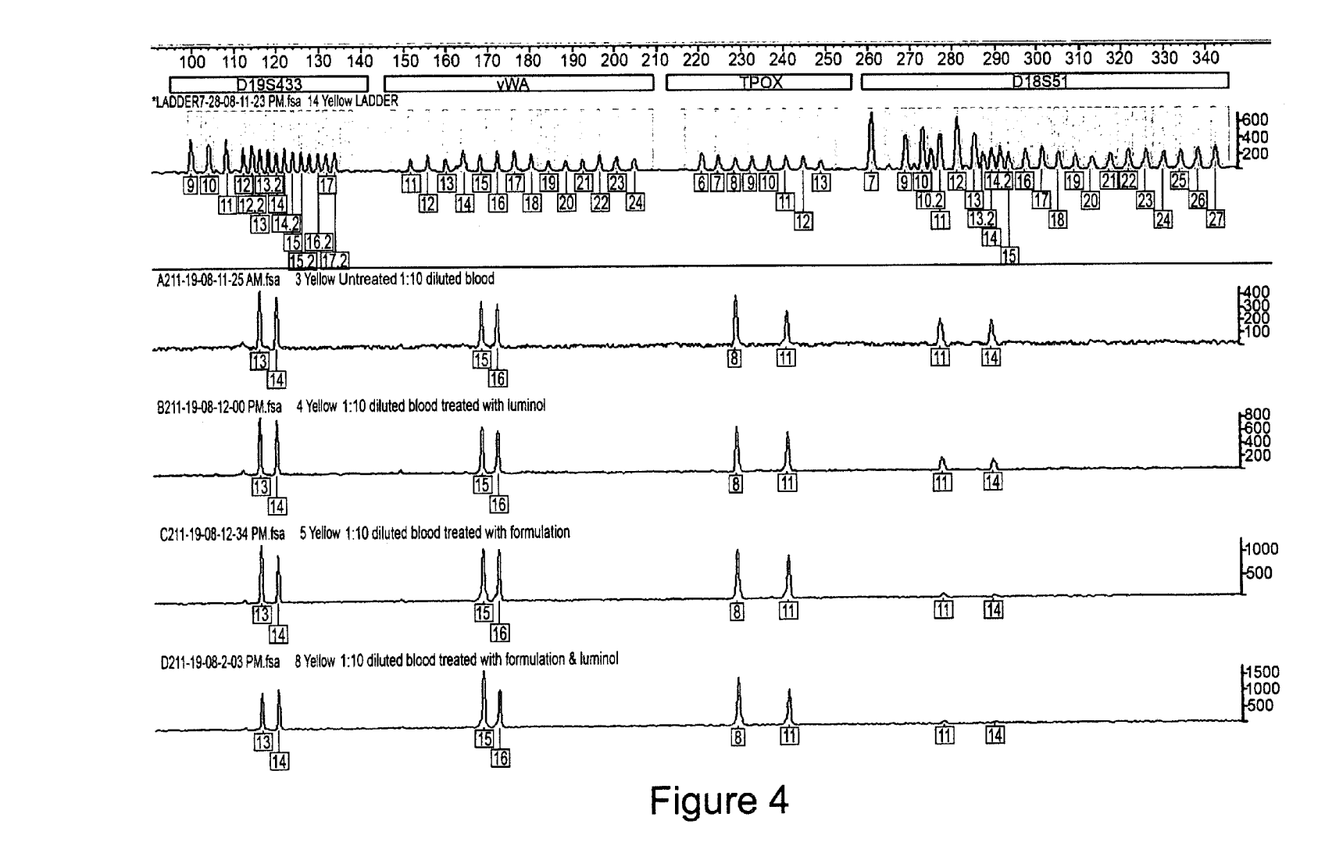
FIG. 4 shows the comparison of electrophoretic runs of samples A; B; C; D; locus: D19S433; V WA; TPOX; D18S51.
Figure 5:
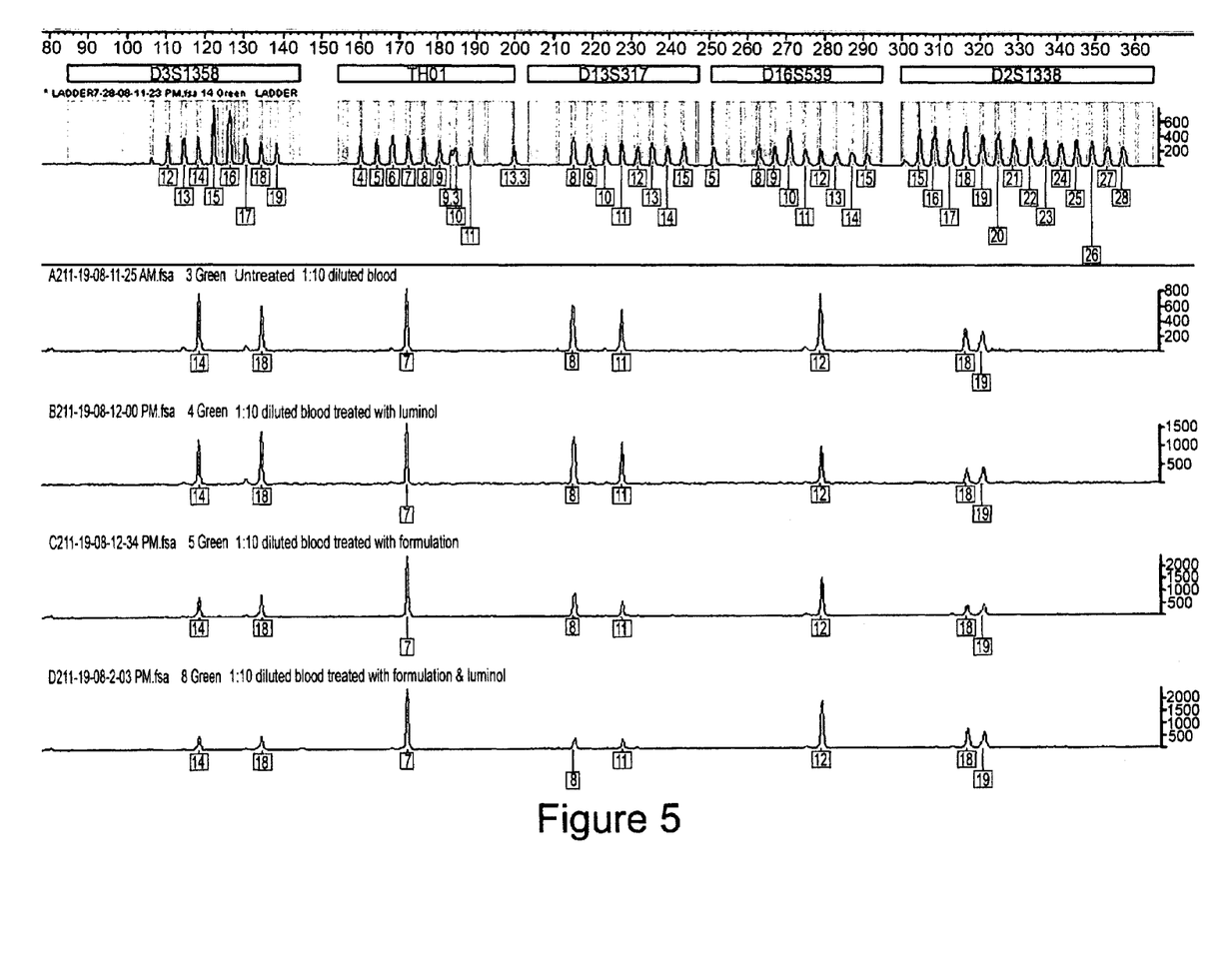
FIG. 5 shows the comparison of the electrophoretic runs of samples A; B; C; D; locus: D3S1358; D165539; D2S1338.

FIG. 2 shows the comparison of the electrophoretic runs of samples A; B; C; D; locus: Amelogenin; D5S818; FGA. FIG. 3 shows the comparison of the electrophoretic runs of samples A; B; C; D; locus: D861179; D21S11. FIG. 4 shows the comparison of the electrophoretic runs of samples A; B; C; D; locus: D19S433; vWA; TPOX; D18S51. FIG. 5 shows the comparison of the electrophoretic runs of samples A; B; C; D; locus: D3S1358; D16S539; D2S1338.

It can be seen that the electrophoretic runs of samples treated with either luminol, TiO$_2$ Anatase suspension (10 m$^2$/g), or suspension and then luminol are all ascribable to the reference genetic profile (non-treated blood) belonging to the male donor from whom the initial blood aliquot was collected. Therefore, it can be concluded that the presence of titanium dioxide does not interfere with the co-amplification procedure for the 15 STR CODIS loci and the Amelogenin locus, on the basis of which it is possible to obtain an unequivocal interpretation of the genetic profile.

The invention claimed is:

1. A method of detecting human or animal blood on a surface, comprising the step of applying to the surface to be investigated a liquid luminol composition comprising a luminol compound, hydrogen peroxide or other peroxidic oxidising agent and an alkaline agent in an amount providing a pH within the range of 10 to 14, characterised in that, prior to said liquid composition, a suspension of inorganic powder selected from the group consisting of silicas, aluminas, titanias, alkaline metal oxides, alkaline earth metal oxides, zinc oxides, zirconias, water insoluble phosphates, micro- and nano-particles of oxide or non oxide semiconductors, functionalised derivatives thereof and mixtures containing varying proportions thereof is applied onto the surface to be investigated, wherein the inorganic powder or the functionalised derivative or the mixture are suspended in an aqueous solvent or in an organic solvent; and wherein the blood comprises haemoglobin which contains iron ions.

2. The method according to claim 1, wherein the suspension is applied to the surface to be investigated by atomization or spraying.

3. The method according to claim 2, wherein the suspension contains from 0.1 to 10 g of powder per 100 ml of solvent.

4. The method according to claim 3, wherein the inorganic powder is titanias, silicas, aluminas, or hydroxiapatite.

5. The method according to claim 1, wherein the luminol compound is 5-amino-2,3-dihydro-1,4-phthalazinedione (luminol) or an isomer, derivative, polymer or precursor thereof capable of emitting chemiluminescence upon oxidation catalysed by the iron ions of blood haemoglobin.

6. The method according to claim 1, wherein the luminol liquid composition comprises luminol at a concentration from 0.01 mM to 4 mM, hydrogen peroxide at a concentration from 1 mM to 20 mM and sodium or potassium hydroxide at a concentration from 0.01 mM to 400 mM.

7. A kit for detecting human or animal blood on a surface, comprising:
- in at least one first vessel, a luminol formulation comprising a luminol compound, hydrogen peroxide or other peroxidic oxidising agent, and an alkaline agent in an amount providing a pH within the range of 10 to 14; and
- in at least one second vessel, a predetermined amount of an inorganic powder selected from the group consisting of silicas, aluminas, titanias, alkaline metal oxides, alkaline earth metal oxides, zinc oxides, zirconias, water insoluble phosphates, micro- and nano-particles of oxide or non oxide semiconductors, functionalised derivatives thereof and mixtures containing varying proportions thereof, wherein the blood comprises haemoglobin which contains iron ions.

8. The kit according to claim 7, wherein the luminol compound, the peroxidic oxidising agent and the alkaline agent are provided as a pre-mixture in a single vessel.

9. The kit according to claim 7, wherein the luminol compound and the peroxidic oxidising agent or the alkaline agent are provided as a pre-mixture in one vessel and the alkaline agent or the peroxidic oxidising agent not included in the pre-mixture is provided in a further vessel.

10. The kit according to claim 7, wherein the luminol compound, the peroxidic oxidising agent and the alkaline agent are each provided in a vessel.

11. The kit according to claim 7, wherein each vessel is a reseleable glass or plastic vessel, a sachet or the cavity of a blister.

12. The kit according to claim 7, wherein the luminol compound is 5-amino-2,3-dihydro-1,4-phthalazinedione (luminol) or an isomer, derivative, polymer or precursor thereof capable of emitting chemiluminescence upon oxidation catalysed by the iron ions of blood haemoglobin.

13. A kit for detecting human or animal blood on a surface, comprising:
- in at least one first vessel, a luminol formulation comprising a luminol compound, hydrogen peroxide or other peroxidic oxidising agent, and an alkaline agent in an amount providing a pH within the range of 10 to 14; and
- in at least one second vessel, a suspension of inorganic powder selected from the group consisting of silicas, aluminas, titanias, alkaline metal oxides, alkaline earth metal oxides, zinc oxides, zirconias, water insoluble phosphates, micro- and nano-particles of oxide or non oxide semiconductors, functionalised derivatives thereof and mixtures containing varying proportions thereof, wherein the inorganic powder, the functionalised derivative or the mixture are suspended in an aqueous solvent or an organic solvent, and wherein the blood comprises haemoglobin which contains iron ions.

14. The kit according to claim 13, wherein the luminol compound, the peroxidic oxidising agent and the alkaline agent are provided as a pre-mixture in a single vessel.

15. The kit according to claim 13, wherein the luminol compound and the peroxidic oxidising agent or the alkaline agent are provided as a pre-mixture in one vessel and the alkaline agent or the peroxidic oxidising agent not included in the pre-mixture is provided in a further vessel.

16. The kit according to claim 13, wherein the luminol compound, the peroxidic oxidising agent and the alkaline agent are each provided in a vessel.

17. The kit according to claim 16, wherein each vessel is a reseleable glass or plastic vessel, a sachet or the cavity of a blister.

18. The kit according to claim 17, wherein the powder suspension contains from 0.1 to 10 g of powder per 100 ml of solvent.

19. The kit according to claim 18, wherein the luminol compound is 5-amino-2,3-dihydro-1,4-phthalazinedione (luminol) or an isomer, derivative, polymer or precursor thereof capable of emitting chemiluminescence upon oxidation catalysed by the iron ions of blood haemoglobin.

20. The kit according to claim 18, wherein the powder suspension is titanias, silicas, aluminas, or hydroxyapatite.

* * * * *